United States Patent
Kabra

(10) Patent No.: US 9,707,173 B2
(45) Date of Patent: Jul. 18, 2017

(54) PHARMACEUTICAL SUSPENSION

(75) Inventor: Bhagwati P. Kabra, Euless, TX (US)

(73) Assignee: Alcon Research, LTD., Fort Worth, TX (US)

(*) Notice: Subject to any disclaimer, the term of this patent is extended or adjusted under 35 U.S.C. 154(b) by 1091 days.

(21) Appl. No.: 12/630,399

(22) Filed: Dec. 3, 2009

(65) Prior Publication Data

US 2010/0144719 A1    Jun. 10, 2010

Related U.S. Application Data

(60) Provisional application No. 61/120,081, filed on Dec. 5, 2008.

(51) Int. Cl.
| | | |
|---|---|---|
| A61K 31/14 | (2006.01) |
| A61K 31/496 | (2006.01) |
| A61K 31/542 | (2006.01) |
| A61K 9/00 | (2006.01) |
| A61K 9/10 | (2006.01) |
| A61K 47/10 | (2017.01) |

(52) U.S. Cl.
CPC .......... *A61K 9/0048* (2013.01); *A61K 9/0043* (2013.01); *A61K 9/0046* (2013.01); *A61K 9/10* (2013.01); *A61K 47/10* (2013.01)

(58) Field of Classification Search
CPC ..... A61K 31/14; A61K 31/452; A61K 31/496
See application file for complete search history.

(56) References Cited

U.S. PATENT DOCUMENTS

| | | |
|---|---|---|
| 3,856,919 A | 12/1974 | Rankin |
| 3,931,319 A | 1/1976 | Green et al. |
| 4,027,020 A | 5/1977 | Green et al. |
| 4,407,791 A | 10/1983 | Stark |
| 4,409,205 A | 10/1983 | Shively |
| 4,525,346 A | 6/1985 | Stark |
| 4,836,986 A | 6/1989 | Ogunbiyi et al. |
| 5,037,647 A | 8/1991 | Chowhan et al. |
| 5,300,287 A | 4/1994 | Park |
| 5,461,081 A | 10/1995 | Ali et al. |
| 5,624,962 A | 4/1997 | Takeuchi et al. |
| 5,756,552 A | 5/1998 | Takeuchi et al. |
| 5,932,572 A | 8/1999 | Dean et al. |
| 6,139,794 A | 10/2000 | Asgharian et al. |
| 6,284,804 B1 | 9/2001 | Singh et al. |
| 6,359,016 B2 | 3/2002 | Singh et al. |
| 6,624,193 B1 * | 9/2003 | Naka et al. ............... 514/546 |
| 6,743,439 B1 * | 6/2004 | Castillo et al. ............... 424/427 |
| 7,001,615 B1 | 2/2006 | Singh et al. |
| 2002/0037877 A1 | 3/2002 | Singh |
| 2003/0139382 A1 | 7/2003 | Wall et al. |
| 2003/0165568 A1 | 9/2003 | Colombo et al. |
| 2004/0256749 A1 | 12/2004 | Chaubal et al. |
| 2005/0245497 A1 | 11/2005 | Penfold et al. |
| 2006/0122277 A1 | 6/2006 | Wong |
| 2006/0134198 A1 | 6/2006 | Tawa et al. |
| 2006/0172969 A1 | 8/2006 | Suzuki et al. |
| 2006/0257486 A1 | 11/2006 | Owen et al. |
| 2006/0257487 A1 | 11/2006 | Owen et al. |
| 2007/0149593 A1 | 6/2007 | Ghosh et al. |
| 2007/0173538 A1 | 7/2007 | Han et al. |
| 2007/0249546 A1 | 10/2007 | Sawaya |

FOREIGN PATENT DOCUMENTS

| | | |
|---|---|---|
| JP | 5155767 | 6/1993 |
| JP | 5186351 | 7/1993 |
| JP | 10287552 | 10/1998 |
| JP | 2000513001 | 10/2000 |
| JP | 2007500226 | 1/2007 |
| JP | 2008531593 | 8/2008 |
| JP | 2008540533 | 11/2008 |
| WO | 91/09523 | 7/1991 |
| WO | 2006/121964 | 11/2006 |
| WO | 2007076358 A1 | 7/2007 |
| WO | 2008076819 A2 | 6/2008 |
| WO | 2009014510 A1 | 1/2009 |
| WO | 2010101971 A1 | 9/2010 |

OTHER PUBLICATIONS

Sigma-Aldrich, poly(ethylene glycol) and poly(ethylene oxide).*
Chemindustry.RU, polyethylene glycol.*
PCT International Search Report for corresponding PCT/US2009/066570 with mailing date Feb. 25, 2011.
PCT International Written Opinion for corresponding PCT/US2009/066570 with mailing date Feb. 25, 2011.
PCT International Preliminary Report on Patentability for PCT/US2009/066570 with mailing date Jun. 16, 2011.
International Pharmaceutical Excipients Council Japan, Pharmaceutical Excipients Directory, 1994, pp. 128-129.
Heitner et al., "Flocculating Agents", Encyclopedia of Chemical Technology, 2004, vol. 11, pp. 623-647.
Rowe et al., "Polyethylene Glycol", Handbook of Pharmaceutical Excipients, 2009, 6th Edition, pp. 517.

* cited by examiner

*Primary Examiner* — Zohreh Fay
(74) *Attorney, Agent, or Firm* — Scott A. Chapple

(57) ABSTRACT

The present invention is directed to the provision of a pharmaceutical suspension. The suspension includes high molecular weight polyethylene glycol as a suspending agent. The suspension also typically includes an antimicrobial agent (e.g., polymeric quaternary ammonium compound), an antimicrobial system (e.g., borate/polyol complex system) or both. The suspension has been found particularly useful as an ophthalmic suspension, but can be used in other instances as well.

26 Claims, No Drawings

PHARMACEUTICAL SUSPENSION

CROSS REFERENCE TO RELATED APPLICATION

This application claims priority under 35 U.S.C. §119 to U.S. Provisional Patent Application No. 61/120,081, filed Dec. 5, 2008, the entire contents of which are incorporated herein by reference.

TECHNICAL FIELD OF THE INVENTION

The present invention is related to pharmaceutical suspensions that include relatively high molecular weight polyethylene glycol, polyethylene oxide or both as a suspending agent. More specifically, the present invention relates to ophthalmic, otic or nasal pharmaceutical suspensions (e.g., multi-dose aqueous ophthalmic suspensions) that include relatively high molecular weight polyethylene glycol, polyethylene oxide or both as a suspending agent and include a therapeutic agent and/or an antimicrobial agent such polymeric quaternary ammonium compound.

BACKGROUND OF THE INVENTION

For many years, the pharmaceutical industry has been developing and discovering suspending agents useful in the preparation of pharmaceutical suspensions. Such suspensions are efficacious for the delivery of therapeutic agents and other uses. These suspensions can be used in a wide variety of applications such as parentral, topical, oral, rectal or the like and, of particular importance to the present invention, ophthalmic, otic and nasal. Examples of such suspensions are described in U.S. Pat. Nos. 7,001,615; 6,359,016; 6,284,804; 6,139,794; 5,932,572; 5,461,081 and US Patent Publication Nos. 20060257487; 20060257486; 20060122277; 20030139382; 20020037877; all of which are incorporated herein by reference for all purposes.

Generally speaking, it is desirable for suspending agent to assist in maintaining a therapeutic agent suspended within a suspension (e.g., an aqueous suspension) for a relatively large amount of time without allowing the therapeutic agent to settle out of the suspension. However, many popular conventional suspending agents allow therapeutic agent to settle out of suspension rather quickly. Moreover, many popular suspending agents also allow the therapeutic agent to become relatively tightly packed within the suspension and may not allow the therapeutic agent to be easily re-suspended. As examples, non-ionic polymers such as hydroxypropyl cellulose and hydroxyethyl cellulose often allow the therapeutic agent to settle out of solution at undesirably high rates and allow the therapeutic agent to become tightly packed once settled.

In addition to the above, many conventionally used suspending agents have been found to be incompatible with ingredients that have recently become desirable within pharmaceutical compositions. As one example, in the ophthalmic industry, there has been a move toward antimicrobial agents such as polymeric quaternary ammonium compounds that exhibit relatively low toxicity, however, certain anionic suspending agents such as carbopol, xanthan gum and carboxymethyl cellulose can be incompatible with such antimicrobial agents under certain circumstances.

In view of the above, there is a need for a suspension and suspending agent that assist the therapeutic agent in remaining suspended in an aqueous or other environment and/or assist the therapeutic agent in resisting tight packing upon settling out of the suspension. Additionally or alternatively, there is a need for suspending agent that exhibits a high degree of compatibility with highly desirable low toxicity ingredients of the suspensions.

SUMMARY OF THE INVENTION

The invention is directed to a pharmaceutical suspension. The suspension includes high molecular weight polyethylene glycol having a molecular weight that is at least 2000, more preferably at least 5,000, even more preferably at least 10,000 and still more preferably at least 20,000, polyethylene oxide or both. The suspension is typically aqueous, although not required unless otherwise stated.

The pharmaceutical suspension will include therapeutic agent. At least a portion of the therapeutic agent will be suspended or suspendable. Examples of such therapeutic agent includes, without limitation, roscovitine, brinzolamide, timolol (e.g., timolol maleate), tandospirone, RTKi, nepafenac, bradykinin related agents (e.g., a bradykinin protein or a bradykinin receptor, antagonist or agonist), anecortave acetate, dexamethasone, any combination thereof or the like. Additionally, the suspensions can include further therapeutic agent such as travoprost, latanoprost, bimatoprost, brimonidine, dorzolamide, moxifloxacin, gattifloxacin, olopatadine, combinations thereof or the like, which may be soluble within the suspension particularly the aqueous portion thereof.

The suspension can be employed as an ophthalmic, otic or nasal suspension. Thus, it can be contacted with the eye, ear, nose or any combination thereof of a human being or other mammal. In one preferred embodiment, the suspension is substantially free of any non-polymeric quaternary ammonium preservatives particularly benzalkonium chloride. The suspension can also include an antimicrobial agent (e.g., polymeric quaternary ammonium compound), an antimicrobial system (e.g., a borate/polyol system) or both.

DETAILED DESCRIPTION OF THE INVENTION

The present invention is predicated upon the provision and use of relatively high molecular weight polyethylene glycol, polyethylene oxide or both as a suspending agent for a pharmaceutical suspension. The pharmaceutical suspension typically includes therapeutic agent, antimicrobial agent or both. The suspending agent is typically employed to form an aqueous suspension. It is contemplated that the suspension of the present invention could be suitable as a parentral, topical, oral or rectal suspension. Additionally or alternatively, the suspension has been found suitable as an otic and/or nasal suspension for application to the ear or nose. The suspension, however, is particularly suitable as an ophthalmic suspension and is quite useful for single or multi-dose topical or other applications to the eye.

Unless otherwise indicated, percentages provided for the ingredients of the suspension of the present invention are weight/volume (w/v) percentages. Those weight/volume percentages are in units of grams per milliliter.

The suspension can include both high molecular weight polyethylene glycol and low molecular weight polyethylene glycol. For the present invention, high molecular weight polyethylene glycol includes any and/or only polyethylene glycols that act as a suspending agent for the pharmaceutical suspension of the present invention. As used herein, the term "suspending agent" refers to polymer that is dispersed or solubilized within a lower density liquid wherein the liquid preferably forms a water based or aqueous solution and wherein the polymer assists in maintaining therapeutic agent suspended (i.e., dispersed) within the liquid vehicle.

Polyethylene glycol (PEG) of the present invention can include any polymer corresponding to equation I below:

$H(OCH_2CH_2)_nOH$ where $n$ is greater than three   Equation I

For high molecular weight PEG, the n of Equation I is typically greater than 50, more typically greater than 100 and even more typically greater than 200.

PEG with average molecular weights such as 2000, 3000, 4000, 6000, 20000 and the like are commercially available and can be employed in the present invention. Preferably, the polyethylene glycol meets United States pharmaceutical standards such as USP31/NF26 and/or European or Japanese standards.

As used herein, Polyethylene Oxide (PEO) is similar to high molecular weight Polyethylene Glycol but has an even higher molecular weight. PEO is a nonionic homopolymer of ethylene oxide, which can be represented by the following formula:

$H-(OCH_2CH_2)_n-OH$ wherein n represents the average number of oxyethylene groups. The molecular weight of PEO utilized in the suspension can range from 100,000 to 8,000,000.

The concentration of high molecular weight PEG, when used in the suspension, is typically at least about 10%, more typically at least about 15% and even more typically at least about 20% and is typically less than 50% and more typically less than 40%. The concentration of PEO, when included, in the suspension is typically at least about 0.1%, more typically at least about 0.5% and even more typically at least about 1%. The concentration of PEO, when included, in the suspension is also typically less than about 10%, more typically less than about 5% and even more typically less than about 3%.

The suspending agent is typically at least 1.0 w/v % (weight/volume percent), more typically at least 4 w/v % and even possibly at least 10% or even at least 22 w/v % of the pharmaceutical suspension. The suspending agent is also typically less than 75 w/v % (weight/volume percent), more typically less than 40 w/v % and even possibly less than 30 or even less than 26 w/v % of the pharmaceutical suspension.

The suspending agent of the present invention will include at least some percentage of polyethylene glycol, polyethylene oxide or both and may be composed multiple different PEGs, multiple different PEOs or both, which may have different molecular weights, different pendant chemical groups or the like. It is also contemplated that the suspending agent may include a mixture of polyethylene glycol, polyethylene oxide or both and one or more other suspension agents such as hydroxypropyl methyl cellulose and hydroxyethyl cellulose.

In a preferred embodiment, the suspending agent is at least 50%, more typically at least 80% and even more typically at least 93% by weight high molecular weight polyethylene glycol, polyethylene oxide or both. It is also contemplated that the suspending agent could be entirely or substantially entirely high molecular weight polyethylene glycol, polyethylene oxide or both. As used herein, the term "substantially entirely" is intended to mean all of a particular ingredient with the exception of a nominal amount.

The viscosity of the suspension will depend upon the concentration and the molecular weight of the PEG, PEO or both included in the suspension. The viscosity of the suspension is typically greater than 5 cps, more typically greater than 15 cps and even more typically greater than 30 cps and even possibly greater than 50 cps. The viscosity of the suspension is typically less than 10000 cps, more typically less than 1000 cps and even more typically less than 500 cps. The viscosity of the suspension for these particular values is measured at a relatively high shear rate in the range of 6 $sec^{-1}$ to 60 $sec^{-1}$ and most preferably at a shear rate of 46 $sec^{-1}$ at room temperature (23° C.).

The density of the suspension is typically greater than 1.005 g/ml, more typically greater than 1.015 g/ml and even more typically greater than 1.020 g/ml.

The volume mean particle size (diameter) of all suspended or suspendable therapeutic agent in the suspension is typically at least 0.1 µm, more typically at least 1.0 µm and even more typically at least 2.0 µm. The volume mean diameter particle size of all suspended or suspendable therapeutic agent in the suspension is typically no greater than 20 µm, more typically no greater than 10 µm and even more typically no greater than 5 µm.

The suspensions of the present invention may contain various types of therapeutic agents. The invention can include therapeutic agents that are nonionic, cationic, anionic or zwitterionic. At least a portion of the therapeutic agent will be suspended or suspendable. Examples of such therapeutic agent includes, without limitation, roscovitine, brinzolamide, timolol, tandospirone, nepafenac, bradykinin related agents (e.g., a bradykinin protein or a bradykinin receptor, antagonist or agonist), anecortave acetate, dexamethasone, any combination thereof or the like. Additionally, the suspensions can include further therapeutic agent such as travoprost, latanoprost, bimatoprost, brimonidine, dorzolamide, moxifloxacin, gattifloxacin, olopatadine, combinations thereof or the like, which may be soluble within the suspension particularly the aqueous portion thereof.

Advantageously, the use of high molecular weight polyethylene glycol as a suspending agent can increase solubility of relatively low solubility therapeutic agents, which may be nonionic. Examples of such agents include, without limitation, roscovotine, brinzolamide, tandospirone, combinations thereof or the like.

The amount of therapeutic agent can vary widely depending upon the type or types of agents employed. Typically, the amount of suspended or suspendable therapeutic agent is at least 0.0001 w/v % (weight/volume percent), more typically at least 0.01 w/v % and even possibly at least 0.1 w/v % of the pharmaceutical suspension. The amount of suspended or suspendable therapeutic agent is also typically less than 10 w/v % (weight/volume percent), more typically less than 5.0 w/v % and even possibly less than 2.0 w/v % of the pharmaceutical suspension.

The suspension of the present invention has been found to be particularly desirable for ophthalmic applications when the therapeutic agent includes, is substantially entirely or is entirely receptor tyrosine kinase inhibitor (RTKi). Thus, in one preferred embodiment, the therapeutic agent can be at least 50%, more typically at least 80% and even more typically at least 95% (e.g., 100%) by weight RTKi.

The preferred RTKi for use in the present invention is a multi-targeted receptor tyrosine kinase inhibitor. Most preferred are RTKi's with multi-target binding profiles, such as N-[4-(3-amino-1H-indazol-4-yl) phenyl]-N'-(2-fluoro-5-methylphenyl)urea, having the binding profile substantially similar to that listed in Table 1 below. Additional multi-targeted receptor tyrosine kinase inhibitors contemplated for use in the compositions of the present invention are described in U.S. application Ser. No. 2004/0235892, incorporated herein by reference for all purposes. As used herein, the term "multi-targeted receptor tyrosine kinase inhibitor" refers to a compound having a receptor binding profile exhibiting selectivity for multiple receptors shown to be important in angiogenesis, such as the profile shown in Table 1, and described in co-pending U.S. application Ser. No. 2006/0189608, incorporated herein by reference for all purposes. More specifically, the preferred binding profile for the multi-targeted receptor tyrosine kinase inhibitor compounds for use in the compositions of the present invention is KDR (VEGFR2), Tie-2 and PDGFR.

The suspensions of the present invention typically include antimicrobial agent. Potential antimicrobial agents include, without limitation, hydrogen peroxide, chlorine containing preservatives such as benzalkonium chloride or others. According to a preferred aspect, however, the pharmaceutical suspension of the present invention is entirely or substantially free of any non-polymeric quaternary antimicrobial agents such as benzalkonium chloride (BAK). Most preferred antimicrobial agent in the pharmaceutical suspension includes polymeric quaternary ammonium compound.

As used herein, the phrase "substantially free of" as it refers to an ingredient of the ophthalmic suspension means that it is contemplated that the ophthalmic solution can be either entirely devoid of that particular ingredient or includes only a nominal amount of that particular ingredient.

The polymeric quaternary ammonium compounds useful in the suspensions of the present invention are those which have an antimicrobial effect and which are ophthalmically acceptable. Preferred compounds of this type are described in U.S. Pat. Nos. 3,931,319; 4,027,020; 4,407,791; 4,525,346; 4,836,986; 5,037,647 and 5,300,287; and PCT application WO 91/09523 (Dziabo et al.). The most preferred polymeric ammonium compound is polyquaternium 1, otherwise known as POLYQUAD® or ONAMERM® with a number average molecular weight between 2,000 to 30,000. Preferably, the number average molecular weight is between 3,000 to 14,000.

The polymeric quaternary ammonium compounds are generally used in the suspensions of the present invention in an amount that is greater than about 0.00001 w/v %, more typically greater than about 0.0003 w/v % and even more typically greater than about 0.0007 w/v % of the suspension. Moreover, the polymeric quaternary ammonium compounds are generally used in the suspensions of the present invention in an amount that is less than about 3 w/v %, more typically less than about 0.003 w/v % and even more typically less than about 0.0015 w/v % of the suspension.

The suspension of the present invention can also include an antimicrobial system such as a borate/polyol complex system. As used herein, the term "borate" shall refer to boric acid, salts of boric acid, borate derivatives and other pharmaceutically acceptable borates, or combinations thereof. Most suitable are: boric acid, sodium borate, potassium borate, calcium borate, magnesium borate, manganese borate, and other such borate salts. Borate interacts with polyols, such as glycerol, propylene glycol, sorbitol and mannitol, to form borate polyol complexes. The type and ratio of such complexes depends on the number of OH groups of a polyol on adjacent carbon atoms that are not in trans configuration relative to each other. It shall be understood that weight/volume percentages of the ingredients polyol and borate include those amounts whether as part of a complex or not.

As used herein, the term "polyol" includes any compound having at least one hydroxyl group on each of two adjacent carbon atoms that are not in trans configuration relative to each other. The polyols can be linear or cyclic, substituted or unsubstituted, or mixtures thereof, so long as the resultant complex is water soluble and pharmaceutically acceptable. Examples of such compounds include: sugars, sugar alcohols, sugar acids and uronic acids. Preferred polyols are sugars, sugar alcohols and sugar acids, including, but not limited to: mannitol, glycerin, xylitol, sorbitol and propylene glycol.

When used, the borate/polyol complex antimicrobial system (i.e., the borate and polyol together) typically comprise at least 0.05 w/v %, more typically at least 0.5 w/v % and even possibly at least 1 or even at least 1.2 w/v % of the suspension and also typically comprise less than 5 w/v %, more typically less than 2.2 w/v % and even possibly less than 1.6 w/v % of the suspension. The borate to polyol ratio (weight to weight ratio) in the suspension is typically between 1 to 1 and 1 to 10 and more typically is between 1 to 2 and 1 to 4 (e.g., about 1 to 3).

In addition to the ingredients above, it is contemplated that a variety of additional or alternative ingredients may be employed in the suspension of the present invention. Other additional therapeutic agents, antimicrobials, suspension agents or the like may be included in the suspension. Other exemplary ingredients possible for the suspension include, without limitation, surfactants, tonicity agents, buffering agents, anti-oxidants, viscosity-modifying agents combinations thereof or the like.

Tyloxapol, polysorbate-80 and polyoxyl hydrogenated castor oil are preferred surfactants. Tyloxapol is a highly preferred surfactant. When used, the surfactant is typically present in a concentration that is at least 0.01 w/v %, more typically at least 0.025 w/v % and even possibly at least 0.1 w/v % of the suspension and also typically is less than 5 w/v %, more typically less than 2.0 w/v % and even possibly less than 1.0 w/v % of the suspension.

The ingredients described herein may be used in forming various types of pharmaceutical suspensions such as ophthalmic, otic and nasal and suspensions, but is particularly useful in ophthalmic suspensions. Examples of such suspensions include: ophthalmic pharmaceutical suspensions, such as topical suspensions used in the treatment of glaucoma, dry eye, infections, allergies or inflammation. The suspensions will typically be aqueous The suspensions of the present invention are typically formulated so as to be compatible with the eye and/or other tissues to be treated with the suspensions. The ophthalmic suspensions intended for direct application to the eye will be formulated so as to have a pH and tonicity that are compatible with the eye.

The compositions will typically have a pH in the range of 4 to 9, preferably 5.5 to 8.5, and most preferably 5.5 to 8.0. Particularly desired pH ranges are 6.0 to 7.8 and more specifically 6.4 to 7.6. The compositions will have an osmolality of 200 to 400 or 450 milliosmoles per kilogram (mOsm/kg), more preferably 240 to 360 mOsm/kg.

The suspensions of the present invention can be ophthalmic suspensions and can particularly be multi-dose ophthalmic suspensions. In that case, the suspensions preferably have sufficient antimicrobial activity to allow the compositions to satisfy the USP preservative efficacy requirements, as well as other preservative efficacy standards for aqueous pharmaceutical compositions.

The preservative efficacy standards for multi-dose ophthalmic solutions in the U.S. and other countries/regions are set forth in the following table:

| | Preservative Efficacy Test ("PET") Criteria (Log Order Reduction of Microbial Inoculum Over Time) | |
|---|---|---|
| | Bacteria | Fungi |
| USP 27 | A reduction of 1 log (90%) by day 7; 3 logs (99.9%) by day 14; and no increase after day 14 | The compositions must demonstrate over the entire test period, which means no increases of 0.5 logs or greater, relative to the initial inoculum. |
| Japan | 3 logs by 14 days; and no increase from day 14 through day 28. | No increase from initial count at 14 and 28 days |
| Ph. Eur. A[1] | A reduction of 2 logs (99%) by 6 hours; 3 logs by 24 hours; and no recovery after 28 days | A reduction of 2 logs (99%) by 7 days, and no increase thereafter |
| Ph. Eur. B | A reduction of 1 log at 24 hours; 3 logs by day 7; and no increase thereafter | A reduction of 1 log (90%) by day 14, and no increase thereafter |
| FDA/ISO 14730 | A reduction of 3 logs from initial challenge at day 14; and a reduction of 3 logs from rechallenge | No increase higher than the initial value at day 14, and no increase higher than the day 14 rechallenge count through day 28. |

[1]There are two preservative efficacy standards in the European Pharmacopoeia: "A" and "B".

The standards identified above for the USP 27 are substantially identical to the requirements set forth in prior editions of the USP, particularly USP 24, USP 25 and USP 26.

Advantageously, it has been found that the suspended and/or suspendable therapeutic agent (drug particles) tends to remain loosely flocculated upon settling such that it can be easily re-suspended when high molecular weight polyethylene glycol and or polyethylene oxide is used as a suspending agent. Without being bound by theory, it is believed that the high molecular weight PEG and/or the PEO interacts with surfactant, the therapeutic agent or both to form the loosely flocculated suspension. Furthermore high molecular weight PEG and/or PEO not only increase viscosity but also raises the density of the suspension such that the solution provides greater resistance to its settling. Unlike anionic polymers such as carbomer 974P, caboxymethyl cellulose or xanthan gum, the high molecular weight PEG and/or PEO is non-ionic and hence is ionically compatible with polymeric quaternary ammonium compounds when those compounds are used as an antimicrobial agent.

It was found that when high molecular weight PEG and/or PEO is used as a suspending agent, the particles form loose floccules, thereby resulting in a high degree of flocculation. The high degree of flocculation of the composition of the present invention ensures that they redisperse or resuspend easily upon gentle shaking.

As used herein, "Degree of Flocculation" means the ratio of final sediment volume (i.e., as a percentage of the total volume) to particle concentration. For example, a suspension with a 1% particle (drug) concentration and a final sediment volume of 8% would have a Degree of Flocculation of 8. Similarly, a suspension composition with a 1% particle concentration and a final sediment volume of 20% would have a Degree of Flocculation of 20, and the same composition with a final sediment volume of 40% would have a Degree of Flocculation of 40.

The final sediment volume is the sediment volume (i.e., percentage of total volume) after prolonged room-temperature storage and does not significantly change with additional storage time. For suspensions of the present invention, the final sediment volume is typically reached in from about three to about twenty one days, however, for testing purposes, a given suspension should be allowed to settle undisturbed for at least one week, more typically at least four weeks and even possibly at least ten weeks.

Sediment volume can be determined as follows: place 10 mL of the suspension composition in a 10 mL graduated cylinder and allow to settle undisturbed for one week. The suspension will then divide into a sediment solution with a sediment volume and a solution volume. The settled sediment will define an upper level or plane within the sediment solution where the sediment stops and the remainder of the suspension is substantially sediment-free solution and that upper level divide the sediment volume from the solution volume. For example, if the sediment show an upper level or plane at the 1 mL mark on the graduated cylinder, it represents a sediment volume of 10%. If the sediment upper level continues to change after one week, additional settling time may be used to get a more accurate measurement.

Typically, the suspensions of the present invention have a Degree of Flocculation that is greater than 4, more typically greater than 8, and even more typically greater than 15.

Before use, suspensions typically need to be redispersed to achieve a more uniform suspension and, in turn, allow for more uniform dosing of the suspended particles. The compositions of this invention will typically be redispersed in no more than 20 seconds, preferably no more than 15 seconds, and most preferably no more than 10 seconds.

Some suspensions within the scope of the present invention can take weeks to months to settle on their own. Therefore, the following method may be employed to more quickly estimate the redispersibility time of a chosen suspension. One milliliter of the suspension composition may be filled into a two milliliter clear glass vial and a rubber stopper and aluminum crimp top may be used to enclose the composition. The filled vial can then be centrifuged for at least 16 hours at 800 rpm (e.g. 48 hours at a relative centrifugal force of about 54 for a higher viscosity suspension). A centrifuge such as the Allegra 21 centrifuge with the Beckman F1010 rotor, which is commercially available from Beckman Coulter, or a comparable centrifuge may be employed. After centrifuging, the vial is then shaken vigorously at 5 second intervals until the particles are dispensed in a substantially homogenous manner.

Table A below provides a listing of exemplary ingredients suitable for an exemplary preferred formulation of the ophthalmic composition of the present invention and desirable weight/volume percentages for those ingredients.

TABLE A

| Ingredient | w/v percent |
|---|---|
| Therapeutic Agent | 1.0 |
| High Molecular Weight PEG | 20 |
| Borate | 0.3 |
| Polyol | 1.0 |
| Surfactant | 0.1 |
| Sodium Chloride | 0.35 |
| polymeric quaternary ammonium compound | 0.001 |
| NaOH/HCl | sufficient to achieve pH = 7.0 |
| purified water | Q.S. 100 |

It is understood that the weight/volume percents in table A can be varied by ±10%, ±20%, ±30%, +90% of those weight/volume percents or more and that those variances can be specifically used to create ranges for the ingredients of the present invention. For example, an ingredient weight/ volume percent of 10% with a variance of +20% means that the ingredient can have a weight/volume percentage range of 8 to 12 w/v %.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

EXAMPLES

Below are provided examples of pharmaceutical (e.g., ophthalmic) suspensions in accordance with the present invention. They are merely examples and do not limit the scope of the invention unless otherwise specifically recited.

Table B below provide one exemplary formulation for a suspension according to the present invention:

TABLE B

| Ingredients | w/v percents |
|---|---|
| Brinzolamide | 1.0 |
| Tyloxapol | 0.2 |
| PEG (molecular weight 20000) | 20 |
| Sodium Chloride | 0.1 |
| Propylene Glycol | 0.75 |
| Mannitol | 0.3 |
| Boric Acid | 0.3 |
| Polyquaternium-1 | 0.001 |
| Sodium Hydroxide or Hydrochloric Acid | Adjust pH to 7.0 |
| Purified Water | QS 100% |

Upon settling, the suspension of table A formed a flocculated sediment that could be easily re-suspended.
PET data for the suspension of table B was as follows:

| | | |
|---|---|---|
| S. Aureus | 6 Hours | 4.9 |
| | 24 Hours | 4.9 |
| | 7 Days | 4.9 |
| | 14 Days | 4.9 |
| | 28 Days | 4.9 |
| Pseudomonas A | 6 Hours | 4.8 |
| | 24 Hours | 4.8 |
| | 7 Days | 4.8 |
| | 14 Days | 4.8 |
| | 28 Days. | 4.8 |
| E. Coli | 6 Hours | 4.9 |
| | 24 Hours | 4.9 |
| | 7 Days | 4.9 |
| | 14 Days | 4.9 |
| | 28 Days. | 4.9 |
| Candida A. | 7 Days | 4.9 |
| | 14 Days | 4.9 |
| | 28 Days. | 4.9 |
| A. Niger | 7 Days | 4.1 |
| | 14 Days | 4.1 |
| | 28 Days. | 3.8 |

Table C below provides another exemplary formulation for a suspension according to the present invention:

TABLE C

| Ingredients | w/v percents |
|---|---|
| Tandospirone Hydrochloride | 1.1 |
| Tyloxapol | 0.1 |
| PEG (molecular weight 20000) | 25 |
| Sodium Chloride | 0.25 |
| Propylene Glycol | 0.75 |
| Mannitol | 0.3 |
| Boric Acid | 0.3 |
| Polyquaternium-1 | 0.001 |
| Sodium Hydroxide or Hydrochloric Acid | Adjust pH to 7.3 |
| Purified Water | QS 100% |

Upon settling, the suspension of table C formed a flocculated sediment that could be easily re-suspended.
PET data for the suspension of table C was as follows:

| | | |
|---|---|---|
| S. Aureus | 6 Hours | 3.9 |
| | 24 Hours | 5.0 |
| | 7 Days | 5.0 |
| | 14 Days | 5.0 |
| | 28 Days | 5.0 |
| Pseudomonas A | 6 Hours | 4.2 |
| | 24 Hours | 5.0 |
| | 7 Days | 5.0 |
| | 14 Days | 5.0 |
| | 28 Days. | 5.0 |
| E. Coli | 6 Hours | 4.9 |
| | 24 Hours | 4.9 |
| | 7 Days | 4.9 |
| | 14 Days | 4.9 |
| | 28 Days. | 4.9 |
| Candida A. | 7 Days | 4.9 |
| | 14 Days | 4.9 |
| | 28 Days. | 4.9 |
| A. Niger | 7 Days | 2.7 |
| | 14 Days | 3.0 |
| | 28 Days. | 2.8 |

Tables D Through G

Tables D and E provide compositions of RTKi with different polymers and surfactants. Examples in Table D were prepared using a 10% RTKi slurry with 1% polysorbate 80, which was ball milled to reduce mean volume particle size to approximately 3 microns. Examples in Table E were prepared using a 10% AL-39324 slurry with 1% tyloxapol, which was ball milled to reduce mean volume particle size to approximately 3 microns. The polymer solutions were either autoclaved or sterile filtered before use to make these compositions. The viscosity, sedimentation volume % upon settling, and redispersibility results of these compositions are provided in Tables F and G. The viscosity was measured using a Brookfield LV viscometer with CP-42 spindle at 12 rpm which produces a shear rate of approximately 46 sec$^{-1}$. Redispersibility time was measured using the procedure provided earlier and centrifuging took place for approximately 16 hours.

The compositions with 15% PEG 20000 or 2.3% PEO 300000 not only settle slowly, but also disperse quickly. While, the compositions with polymer hydroxypropyl methyl cellulose (HPMC) and hydroxyethyl cellulose (HEC) have desirable viscosity and settle relatively slowly, these compositions do not redisperse uniformly within 30 seconds. Thus compositions with PEG 20000 or PEO 300000 have preferably suspension characteristics.

TABLE D

| Ingredients | w/v percents | w/v percents | w/v percents | w/v percents | w/v percents | w/v percents | w/v percents | w/v percents |
|---|---|---|---|---|---|---|---|---|
| RTKi | 1 | 1 | 1 | 1 | 1 | 1 | 1 | 1 |
| Polysorbate 80 | 0.1 | 0.1 | 0.1 | 0.1 | 0.1 | 0.1 | 0.1 | 0.1 |
| HPMC | — | 0.6 | — | — | — | — | — | — |
| HEC | — | — | 0.4 | — | — | — | — | — |
| PEG 400 | — | — | — | 15 | — | — | — | — |
| PEG 3000 | — | — | — | — | 15 | — | — | — |
| PEG 20000 | — | — | — | — | — | 5 | 15 | — |
| PEG 300000 | — | — | — | — | — | — | — | 2.3 |
| Sodium Chloride | 0.3 | 0.3 | 0.3 | 0.3 | 0.3 | 0.3 | 0.3 | 0.3 |
| Boric Acid | 0.3 | 0.3 | 0.3 | 0.3 | 0.3 | 0.3 | 0.3 | 0.3 |
| Mannitol | 0.3 | 0.3 | 0.3 | 0.3 | 0.3 | 0.3 | 0.3 | 0.3 |
| Propylene Glycol | 0.75 | 0.75 | 0.75 | 0.75 | 0.75 | 0.75 | 0.75 | 0.75 |
| Polyquaternium-1 | 0.001 | 0.001 | 0.001 | 0.001 | 0.001 | 0.001 | 0.001 | 0.001 |
| Sodium Hydroxide or Hydrochloric Acid | Adjust pH 7.0 | Adjust pH 7.0 | Adjust pH 7.0 | Adjust pH 7.0 | Adjust pH 7.0 | Adjust pH 7.0 | Adjust pH 7.0 | Adjust pH 7.0 |
| Purified Water | QS | QS | QS | QS | QS | QS | QS | QS |

TABLE E

| Ingredients | w/v percents | w/v percents | w/v percents | w/v percents | w/v percents | w/v percents | w/v percents | w/v percents |
|---|---|---|---|---|---|---|---|---|
| RTKi | 1 | 1 | 1 | 1 | 1 | 1 | 1 | 1 |
| Tyloxapol | 0.1 | 0.1 | 0.1 | 0.1 | 0.1 | 0.1 | 0.1 | 0.1 |
| HPMC | — | 0.6 | — | — | — | — | — | — |
| HEC | — | — | 0.4 | — | — | — | — | — |
| PEG 400 | — | — | — | 15 | — | — | — | — |
| PEG 3000 | — | — | — | — | 15 | — | — | — |
| PEG 20000 | — | — | — | — | — | 5 | 15 | — |
| PEG 300000 | — | — | — | — | — | — | — | 2.3 |
| Sodium Chloride | 0.3 | 0.3 | 0.3 | 0.3 | 0.3 | 0.3 | 0.3 | 0.3 |
| Boric Acid | 0.3 | 0.3 | 0.3 | 0.3 | 0.3 | 0.3 | 0.3 | 0.3 |
| Mannitol | 0.3 | 0.3 | 0.3 | 0.3 | 0.3 | 0.3 | 0.3 | 0.3 |
| Propylene Glycol | 0.75 | 0.75 | 0.75 | 0.75 | 0.75 | 0.75 | 0.75 | 0.75 |
| Polyquaternium-1 | 0.001 | 0.001 | 0.001 | 0.001 | 0.001 | 0.001 | 0.001 | 0.001 |
| Sodium Hydroxide or Hydrochloric Acid | Adjust pH 7.0 | Adjust pH 7.0 | Adjust pH 7.0 | Adjust pH 7.0 | Adjust pH 7.0 | Adjust pH 7.0 | Adjust pH 7.0 | Adjust pH 7.0 |
| Purified Water | QS | QS | QS | QS | QS | QS | QS | QS |

TABLE F (Results of compositions in Table D with 0.1% Polysorbate 80)

| | Polymer | | | | | | | |
|---|---|---|---|---|---|---|---|---|
| | None | 0.6% HPMC | 0.4% HEC | 15% PEG 400 | 15% PEG 3000 | 5% PEG 20000 | 15% PEG 20000 | 2.3% PEO 300,000 |
| Viscosity (cps) | 1.1 | 24.4 | 41.9 | 2.8 | 5 | 5 | 31.8 | 33.8 |
| Redispersibility | 5 | >30 | >30 | 5 | 10 | 10 | 10 | 15 |
| Sedimentation Volume % | | | | | | | | |
| at 0 Hour | 100 | 100 | 100 | 100 | 100 | 100 | 100 | 100 |
| at 1 Hour | 100 | 100 | 100 | 44 | 96 | 92 | 100 | 100 |
| at 2 Hours | 98 | 100 | 100 | 40 | 82 | 70 | 100 | 100 |
| at 1 Day | 8 | 100 | 100 | 36 | 16 | 14 | 96 | 100 |
| at 1 Week | 6 | 18 | 100 | 36 | 10 | 6 | 18 | 18 |

TABLE G (Results of compositions in Table E with 0.1% tyloxapol)

| | Polymer | | | | | | | |
|---|---|---|---|---|---|---|---|---|
| | None | 0.6% HPMC | 0.4% HEC | 15% PEG 400 | 15% PEG 3000 | 5% PEG 20000 | 15% PEG 20000 | 2.3% PEO 300,000 |
| Viscosity (cps) | 1.3 | 26.3 | 46.4 | 2.2 | 4.9 | 5.5 | 33.6 | 36.7 |
| Redispersibility | 5 | >30 | >30 | 5 | 5 | 5 | 5 | 10 |
| Sedimentation Volume % | | | | | | | | |
| at 0 Hour | 100 | 100 | 100 | 100 | 100 | 100 | 100 | 100 |
| at 1 Hour | 94 | 100 | 100 | 100 | 94 | 92 | 100 | 100 |
| at 2 Hours | 88 | 100 | 100 | 96 | 84 | 72 | 100 | 100 |
| at 1 Day | 34 | 100 | 100 | 24 | 18 | 18 | 98 | 86 |
| at 1 Week | 32 | 98 | 100 | 22 | 10 | 12 | 24 | 36 |

I claim:

1. A pharmaceutical suspension, comprising:
an aqueous solution that includes high molecular weight polyethylene glycol, polyethylene oxide or both as a suspending agent, the high molecular weight polyethylene glycol, when included, having a molecular weight that is at least 2000; and
a therapeutic agent that is suspended by the high molecular weight polyethylene glycol, polyethylene oxide or both within the solution wherein:
  i. the polyethylene oxide, when included in the suspension, is in the suspension at a concentration that is at least 0.5 w/v % but less that 10 w/v % and has a molecular weight of 100,000 to 8,000,000; and
  ii. the polyethylene glycol, when included in the suspension, is in the suspension at a concentration that is at least 15 w/v % but less that 50 w/v %.

2. A pharmaceutical suspension as in claim 1 wherein the therapeutic agent is selected from roscovitine, brinzolamide, tandospirone, anecortave acetate, bradykinin related agents, dexamethasone, nepafenac, any combination thereof.

3. A pharmaceutical suspension as in claim 1 further comprising a second therapeutic agent which is soluble or solubilized in the formulation.

4. A pharmaceutical suspension as in claim 3 wherein the second therapeutic agent is travoprost, latanoprost, bimatoprost, dorzolamide, timolol, brimonidine, moxifloxacin or a combination thereof.

5. A pharmaceutical suspension as in claim 1 wherein the suspension has a degree of flocculation of at least 10.

6. A pharmaceutical suspension as in claim 1 wherein the suspension is an ophthalmic, otic or nasal suspension.

7. A pharmaceutical suspension as in claim 6 wherein the suspension is an ophthalmic suspension.

8. A pharmaceutical suspension as in claim 1 wherein the suspension is substantially free of any non-polymeric quaternary ammonium compound, particularly BAK.

9. A pharmaceutical suspension as in claim 1 further comprising an antimicrobial agent.

10. A pharmaceutical suspension as in claim 9 wherein the antimicrobial agent includes polymeric quaternary ammonium compound.

11. A pharmaceutical suspension as in claim 10 further comprising borate, polyol or both.

12. A pharmaceutical suspension as in claim 11 wherein the borate is boric acid.

13. A pharmaceutical suspension as in either claim 12 wherein the polyol is selected from glycerol, propylene glycol, mannitol, sorbitol or any combination thereof and the polyol forms a borate/polyol complex in the suspension.

14. A pharmaceutical suspension as in claim 1 wherein the concentration of polyethylene oxide, when included in the suspension, is at least 1.0 w/v %.

15. A pharmaceutical suspension as in claim 1 wherein the high molecular weight polyethylene glycol has a molecular weight that is at least 10,000.

16. A pharmaceutical suspension as in claim 1 wherein the viscosity of the suspension is greater than 15 cps but no greater than 1000 cps wherein the viscosity of the suspension is measured at a high shear rate of 46 sec-1 at room temperature.

17. A pharmaceutical suspension as in claim 1 wherein the density of the suspension is greater than 1.015 cps.

18. A pharmaceutical suspension as in claim 1 wherein the suspension includes a surfactant.

19. A pharmaceutical suspension as in claim 18 wherein the surfactant is tyloxapol.

20. A suspension as in claim 1 wherein the volume mean diameter particle size of any suspended or suspendable therapeutic agent in the suspension is typically at least 0.1 μm but no greater than 20 μm.

21. A pharmaceutical suspension, comprising:
an aqueous solution that includes high molecular weight polyethylene glycol, polyethylene oxide or both as a suspending agent, the high molecular weight polyethylene glycol, when included, having a molecular weight that is at least 2000; and
therapeutic agent that is suspended by the high molecular weight polyethylene glycol, polyethylene oxide or both within the solution;
wherein the suspension has a degree of flocculation of at least 10;
wherein the suspension is an ophthalmic, otic or nasal suspension;
wherein the viscosity of the suspension is greater than 15 cps but no greater than 1000 cps wherein the viscosity of the suspension is measured at a high shear rate of 46 sec-1 at room temperature;
wherein the polyethylene oxide, when included in the suspension, is in the suspension at a concentration that is at least 0.5 w/v % but less that 10 w/v % and has a molecular weight of 100,000 to 8,000,000; and
wherein the polyethylene glycol, when included in the suspension, is in the suspension at a concentration that is at least 15 w/v % but less that 50 w/v %.

22. A pharmaceutical suspension as in claim 21 wherein the suspension is an ophthalmic suspension.

23. A pharmaceutical suspension as in claim 22 wherein the concentration of polyethylene oxide, when included in the suspension, is at least 1.0 w/v %.

24. A pharmaceutical suspension as in claim 1 wherein the suspending agent consists essentially of polyethylene oxide, the polyethylene glycol or a combination thereof.

25. A pharmaceutical suspension as in claim 21 wherein the suspending agent consists essentially of polyethylene oxide, the polyethylene glycol or a combination thereof.

26. A pharmaceutical suspension as in claim 25 wherein the suspension includes a polymeric quaternary ammonium compound.

* * * * *